(12) United States Patent
Vlaskamp et al.

(10) Patent No.: US 10,791,608 B2
(45) Date of Patent: Sep. 29, 2020

(54) LIGHTING CONTROL

(71) Applicant: SIGNIFY HOLDING B.V., Eindhoven (NL)

(72) Inventors: Björn Nicolaas Servatius Vlaskamp, S-Hertogenbosch (NL); Jan Souman, Helmond (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 16/477,678

(22) PCT Filed: Jan. 10, 2018

(86) PCT No.: PCT/EP2018/050519
§ 371 (c)(1),
(2) Date: Jul. 12, 2019

(87) PCT Pub. No.: WO2018/130546
PCT Pub. Date: Jul. 19, 2018

(65) Prior Publication Data
US 2019/0364643 A1 Nov. 28, 2019

(30) Foreign Application Priority Data

Jan. 12, 2017 (EP) .................................... 17151220

(51) Int. Cl.
*H05B 37/02* (2006.01)
*H05B 39/04* (2006.01)
(Continued)

(52) U.S. Cl.
CPC .......... *H05B 47/105* (2020.01); *A61M 21/02* (2013.01); *H05B 47/11* (2020.01); *H05B 47/16* (2020.01);
(Continued)

(58) Field of Classification Search
None
See application file for complete search history.

(56) References Cited

U.S. PATENT DOCUMENTS

| | | |
|---|---|---|
| 5,993,000 A | 11/1999 | Kobayashi et al. |
| 7,744,216 B1 | 6/2010 | Uhlhorn |

(Continued)

FOREIGN PATENT DOCUMENTS

| | | |
|---|---|---|
| CN | 105759457 A | 7/2016 |
| WO | 2014123781 A1 | 8/2014 |
| WO | 2015072202 A1 | 5/2015 |

OTHER PUBLICATIONS

Anne-Marie Chang, et al., "Evening Use of Light-Emitting Ereaders Negatively Affects Sleep, Circadian Timing, and Next-Morning Alterness," PNAS, Jan. 2015, vol. 112, No. 4 (6 Pages).
(Continued)

*Primary Examiner* — Anh Q Tran
(74) *Attorney, Agent, or Firm* — Meenakshy Chakravorty (57) ABSTRACT

According to a first aspect disclosed herein, there is provided a controller for controlling a first light source to emit light into a pupil of a human user in order to reduce at least one biological effect of light from a second light source on the human user, the controller comprising: a first input for receiving light property data indicating a property of the light from the second light source, said property being of a type which causes a biological effect on the human user; a second input for receiving pupil data indicating a size of the pupil of the human user; an output for sending control commands to the first light source; a processor configured to: determine, using the light property data received via the first input, that the light from the second light source has said property; in response to said determination that the light from the second light source has said property, determine, using said pupil data received via the second input, a current
(Continued)

size of the pupil; and on condition that the current size of the pupil is determined to be larger than a minimum size, control the first light source to emit light not having said property into the pupil and thereby reduce the size of the pupil.

15 Claims, 4 Drawing Sheets

(51) Int. Cl.
    *H05B 41/36*     (2006.01)
    *H05B 47/105*     (2020.01)
    *A61M 21/02*     (2006.01)
    *H05B 47/11*     (2020.01)
    *H05B 47/16*     (2020.01)
    *A61M 21/00*     (2006.01)

(52) U.S. Cl.
    CPC ............... *A61M 2021/0044* (2013.01); *A61M 2210/0612* (2013.01)

(56) References Cited

U.S. PATENT DOCUMENTS

| 8,319,804 | B2 | 11/2012 | Kuo | |
|---|---|---|---|---|
| 9,289,622 | B2 | 3/2016 | Feng et al. | |
| 2010/0174345 | A1 | 7/2010 | Ashdown | |
| 2010/0244740 | A1 | 9/2010 | Alpert et al. | |
| 2012/0259392 | A1* | 10/2012 | Feng | H05B 47/11 607/88 |
| 2015/0097490 | A1* | 4/2015 | Okuya | H05B 47/105 315/158 |
| 2016/0199000 | A1* | 7/2016 | Gimenez | G01J 1/0271 315/151 |
| 2016/0231573 | A1 | 8/2016 | Mullins et al. | |
| 2016/0341436 | A1* | 11/2016 | Parker | H05B 45/20 |

OTHER PUBLICATIONS

Ji Hye Oh, et al., "Analysis of Circadian Properties and Healthy Levels of Blue Light From Smartphones at Night," Scientific Reports, 2015 (9 Pages).

* cited by examiner

LIGHTING CONTROL

CROSS-REFERENCE TO PRIOR APPLICATIONS

This application is the U.S. National Phase application under 35 U.S.C. § 371 of International Application No. PCT/EP2018/050519, filed on Jan. 10, 2018, which claims the benefit of European Patent Application No. 17151220.5, filed on Jan. 12, 2017. These applications are hereby incorporated by reference herein.

TECHNICAL FIELD

The present disclosure relates to systems and methods for managing biological effects of a lighting device on a user.

BACKGROUND

Different parts of the light spectrum are known to have effects on human behaviour and well-being. This is particularly true for light entering the human eye, where the light can cause both physiological effects (e.g. circadian rhythm regulation) and psychological effects (e.g. a relaxing atmosphere). For example, the blue part of the spectrum (around 480 nm) is known to affect circadian rhythm, alertness and quality of sleep, and is used in light therapy for the treatment of conditions such as Seasonal Affective Disorder (SAD).

The term "colour temperature" is a known term. The colour temperature of a light source is equal to the temperature of an ideal black-body radiator which produces a comparable hue to the light source, usually expressed in Kelvin. A higher colour temperature light source outputs more light in the blue part of the spectrum.

US 2016/341436 A1 discloses a method comprising: (a) receiving a set of physiological data associated with at least one health condition of a human subject; (b) receiving a set of environmental data associated with one or more environment conditions to which the human subject is or has been exposed; (c) determining a set of operating parameters for at least one environmental device based at least partially on at least a portion of the set of physiological data and at least a portion of the set of environmental data; and (d) transmitting the set of operating parameters to the at least one environmental device to at least partially control at least one controlled environmental condition to which the human subject is exposed to thereby at partially control the at least one health condition. In particular, the health condition controlled is a circadian biorhythm of the human subject.

SUMMARY

Many light sources such as LED screens in laptops or tablets have a lot of energy in the blue part of the spectrum. Staring into these devices may thus have negative consequences on behaviour and well-being, in particular when used at night before going to bed. Conversely, these devices can also be used for treatments of disorders as outlined above.

A major question is how the unwanted or undesired effects of blue light coming from these devices can be limited.

Existing solutions either change the light coming from the screen or filter it at the eye. For instance, computer applications (e.g. f.lux) changes the colour temperature of a display screen depending on the time of day. Also, special (orange tinted) glasses can be used to filter out the blue part of the spectrum. Both types of solution (glasses or f.lux) change the appearance of the light coming from the screen (it looks yellowish or even orange).

In contrast to the prior art solutions, the present invention adds light external to the light emitting device to reduce the negative impact of blue light in an adaptive way. The idea is based on the knowledge that the pupil size is directly influenced by the amount of light incident on the eyes i.e. more light results in a smaller pupil size. The pupil regulates the amount of light in the eye and most importantly at the photo-sensitive part of the eye: the retina. A smaller pupil size reduces the light incidence. By adding external light not having the blue part of the spectrum, the resulting reduction in pupil size reduces the total amount of blue light at the retina (even though there is overall more light). A human pupil has a minimum size which is typically around 2 mm in diameter.

However, in particular at night people prefer to have low light levels. By changing the ambient light levels depending on the blue light falling on the eye (no light is added when there is no blue light hitting the eye) and the pupil diameter (if it is already small adding addition light will not be of benefit) a balance can be found between low light levels and a reduction of blue light at the retina. Even though the overall composition of the light spectrum reaching the eyes changes because of the additional light source, the colour coming from the device (such as a tablet device) remains perceptually identical (colour constancy). An advantage of the disclosed system/method therefore is that the biologic effect of the light emitted from a device (such as a tablet device) is decreased without changing the properties (in terms of e.g. spectral power distribution or intensity) of the light emitted from the device. This is especially advantageous for use of display devices (such as mobile devices, tablets, computer screens or television screens) that are not controllable in terms of light settings such as brightness or color temperature or of which the user prefers not to change these light settings for reasons of comfortable reading/viewing.

According to a first aspect disclosed herein, there is provided a controller for controlling a first light source to emit light into a pupil of a human user in order to reduce at least one biological effect of light from a second light source on the human user, the controller comprising: a first input for receiving light property data indicating a property of the light from the second light source, said property being of a type which causes a biological effect on the human user; a second input for receiving pupil sensor data from a pupil sensor detecting a size of the pupil of the human user; an output for sending control commands to the first light source; and a processor configured to: (i) determine, using the light property data received via the first input, that the light from the second light source has said property; (ii) in response to said determination that the light from the second light source has said property, determine, using said pupil sensor data received via the second input, a current size of the pupil; and (iii) on condition that the current size of the pupil is determined to be larger than a minimum size, control the first light source to emit light not having said property into the pupil and thereby reduce the size of the pupil.

Even if the second light source is not controllable by the controller, the first light source can be controlled to compensate for light emitted by the uncontrollable second light source.

In embodiments, said controlling the light output of the first light source comprises increasing the brightness of the light output of the first light source, in particular, the luminous intensity of the light (i.e. the intensity within the visible spectrum).

In embodiments, said data indicating a property of the light from the second light source is received from a light sensor detecting the property of the light from the second light source.

In embodiments, said data indicating a property of the light from the second light source is received from a database storing properties of the second light source.

In embodiments, said property is a substantial luminance in a blue part of the visible spectrum. "Substantial" in this context means a sufficiently high relative intensity of the blue part of the visible spectrum to induce physiological effects associated with blue light. That is, the intensity of a blue part of the spectrum (in embodiments above about 450 nm) is sufficiently high relative to the rest of the visible spectrum to induce such physiological effects.

In embodiments, the processor is arranged to perform said control of the first light source based on a time constant specifying a transition time from a first light output setting of the first light source to a second light output setting of the first light source.

In embodiments, the second light source is a screen of a computing device.

In embodiments, the second light source is a luminaire arranged to illuminate an environment of the human user.

In embodiments, the pupil data are received from a pupil sensor (302) detecting the size of the pupil of the human user.

In embodiments, the pupil sensor is a camera arranged to capture an image of the pupil of the human user.

In embodiments, the camera is integrated into a user device of the human user.

In embodiments, the controller and first light source form a sub-system ("compensatory system") which may be selectively turned on and off by the human user.

According to a second aspect disclosed herein, there is provided a user device comprising the controller according to the first aspect and a camera, wherein the camera is a front-facing camera integrated into the user device.

In embodiments, the first light source is a light source separate from the user device. For example, the first light source may be integrated into a device other than the user device comprising the camera (such as a second user device different e.g. a wearable headset), or may be another light source separate from the user device such as a luminaire arranged to illuminate an environment of the user.

According to a third aspect disclosed herein, there is provided a system comprising the user device and the first light source.

According to a fourth aspect disclosed herein, there is provided a method of controlling a first light source to emit light into a pupil of a human user in order to reduce at least one biological effect of light from a second light source on the human user, the method comprising: (i) receiving light property data indicating a property of the light from the second light source, said property being of a type which causes a biological effect on the human user; (ii) receiving pupil data indicating a size of the pupil of the human user; (iii) determining, using the light property data, that the light from the second light source has said property; (iv) in response to said determination that the light from the second light source has said property, determine, using said pupil data, a current size of the pupil; and (v) on condition that the current size of the pupil is determined to be larger than a minimum size, controlling the first light source to emit light not having said property into the pupil and thereby reducing the size of the pupil.

According to another aspect disclosed herein, there is provided a computer program product comprising computer-executable code embodied on a computer-readable storage medium arranged so as when executed by one or more processing units to perform the method according to any the fourth aspect.

BRIEF DESCRIPTION OF THE DRAWINGS

To assist understanding of the present disclosure and to show how embodiments may be put into effect, reference is made by way of example to the accompanying drawings in which.

DETAILED DESCRIPTION OF EMBODIMENTS

Figure 1:
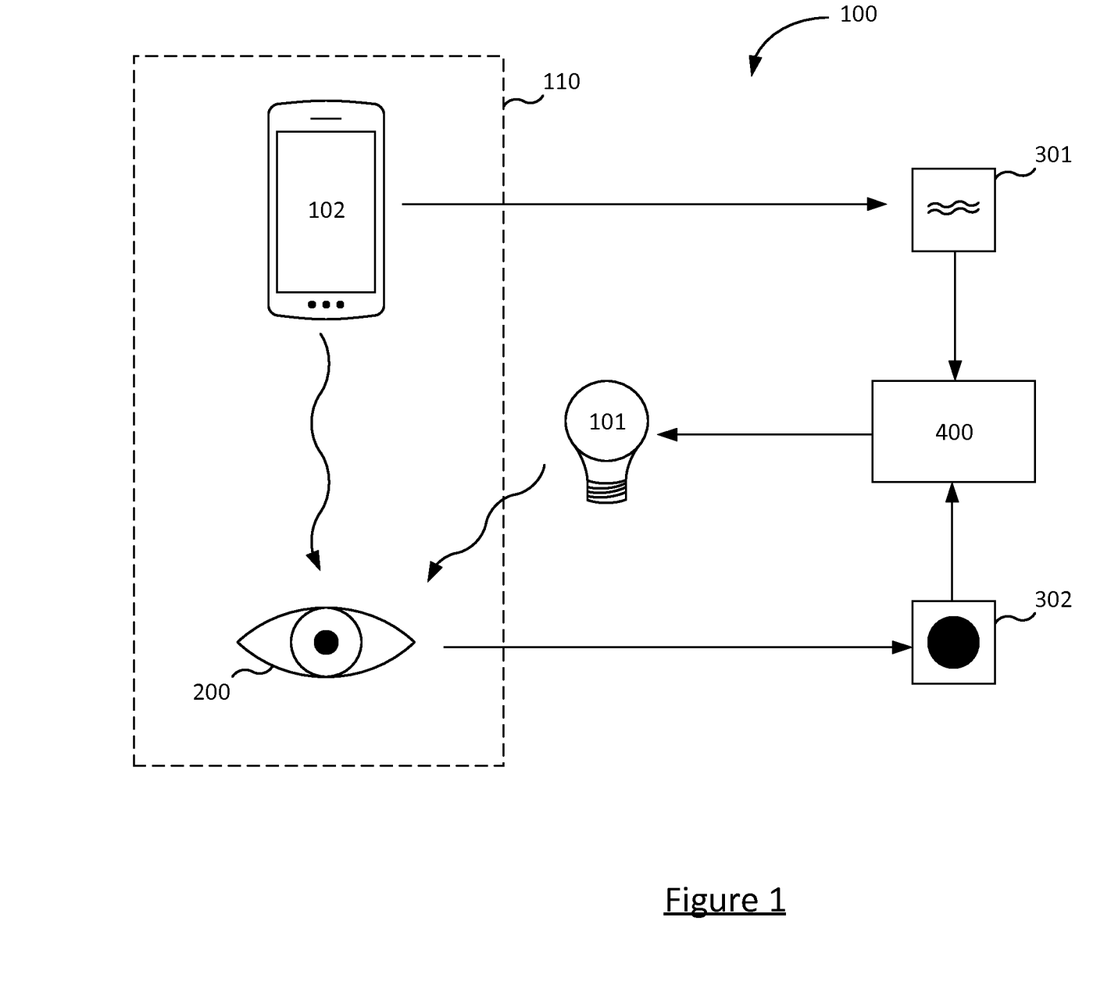
FIG. 1 shows a system according to embodiments of the present invention.

FIG. 1 shows a system according to embodiments of the present invention. The system comprises a first light source 101, a second light source 102, a light sensor 301, a pupil sensor 302, and a controller 400. Also shown is a human eye 200.

The second light source 102 may be any device which produces a light output and hence may be a dedicated lighting device such as a luminaire (e.g. an incandescent bulb, fluorescent bulb, LED luminaire etc.) or may be a device which produces a light output but has a primary purpose other than illumination (e.g. a computer screen or screen of a mobile device as shown in FIG. 1).

The second light source 102 is arranged such that light output from the second light source 102 enters the eye 200 via the pupil of the eye 200. Together, the second light source 102 and the eye 200 represent a "sub-system" 110 which is commonplace. As mentioned above, light from the second light source 102 entering the eye 200 of a human being or a user may create a biological effect (either physiological or psychological) on the user.

The biological effect of the second light source 102 may be either wanted or unwanted by the user. The present invention allows for the decreasing of unwanted effects from the second light source 102 even when the second light source 102 is not directly controllable by the user. Throughout this disclosure, the terms wanted and unwanted may be also interpreted as desired or undesired. That is, the second light source 102 may be part of an entirely separate lighting system over which the user has no control. In these cases, the user may wish to decrease an unwanted effect of the lighting but may have no means by which to alter the settings of the second light source 102. The present invention nevertheless allows the user to decrease the unwanted effect of the second lighting source 102 by way of the further elements in FIG. 1 described below.

A controller 400 is provided which receives input from a light sensor 301 and a pupil sensor 302, and generates control commands for controlling the first light source 101.

The first light source 101 may comprise one or more individual lighting devices such as LEDs, incandescent or fluorescent bulbs etc. The first light source 101 can be a lamp, but can also be a light source of any other device (e.g. a connected device such as a smart phone) with multiple relatively narrowband LED's or colour filters, for example a TV which emits a combination of green and red light.

The light sensor 301 measures the power spectrum of the light hitting the eye 200 from the second light source 102. E.g. the light sensor 301 measures the amount of blue light in the spectrum of the light output by the second light source 102. In case the light sensor 301 is arranged such that it also detects light from the first light source 101, the contribution from the first light source 101 can be removed from the sensor readings using knowledge of the output properties of the first light source 101 (which are readily available to the system as the first light source 101 is controlled by the system).

The pupil sensor 302 measures the size of the pupil of the user's eye 200. The pupil sensor 302 may comprise a camera for taking an image of the user's eye 200, from which a size of the pupil can be determined using known image processing techniques. The camera may be a visible light camera but may also be a (near-) infrared camera, and an estimate of the pupil size can be determined based on reflected light from the eye 200. That is, light can be directed to the eye 200 and the amount of light returned/reflected by the eye 200 can be measured as an indication of pupil size, based on the fact that the pupil is black and most light falling onto the pupil will pass through it. The larger the pupil, the less light is reflected. Again, techniques for doing so are well-known in the art.

The controller 400 drives the first light source 101 depending on the data coming from the sensors 301, 302. The controller 400 determines the spectral output of the first light source 101 that is required to reduce the unwanted effects from the light originating from the second light source 102.

The controller 400 increases the light intensity or brightness of the blue deprived light from the first light source 101 when there is excessive or too much blue light from the second light source 102 hitting the eye (as measured by the light sensor 301) but only if pupil diameter is larger than a minimum size. The blue deprive light from the first light source 101 can be provided so that there is minimal or no change to the ambient lighting settings, e.g. by means of a dedicated light source close to or in proximity of the user such as a spot light or reading light or close to or in proximity of the eye(s) of the user such as integrated in glasses or another wearable device.

Note that information regarding whether or not the effect is wanted can be provided to the controller 400 by the user, e.g. via a user device described later, and stored in memory by the controller 400 as described in more detail below.

Figure 2:
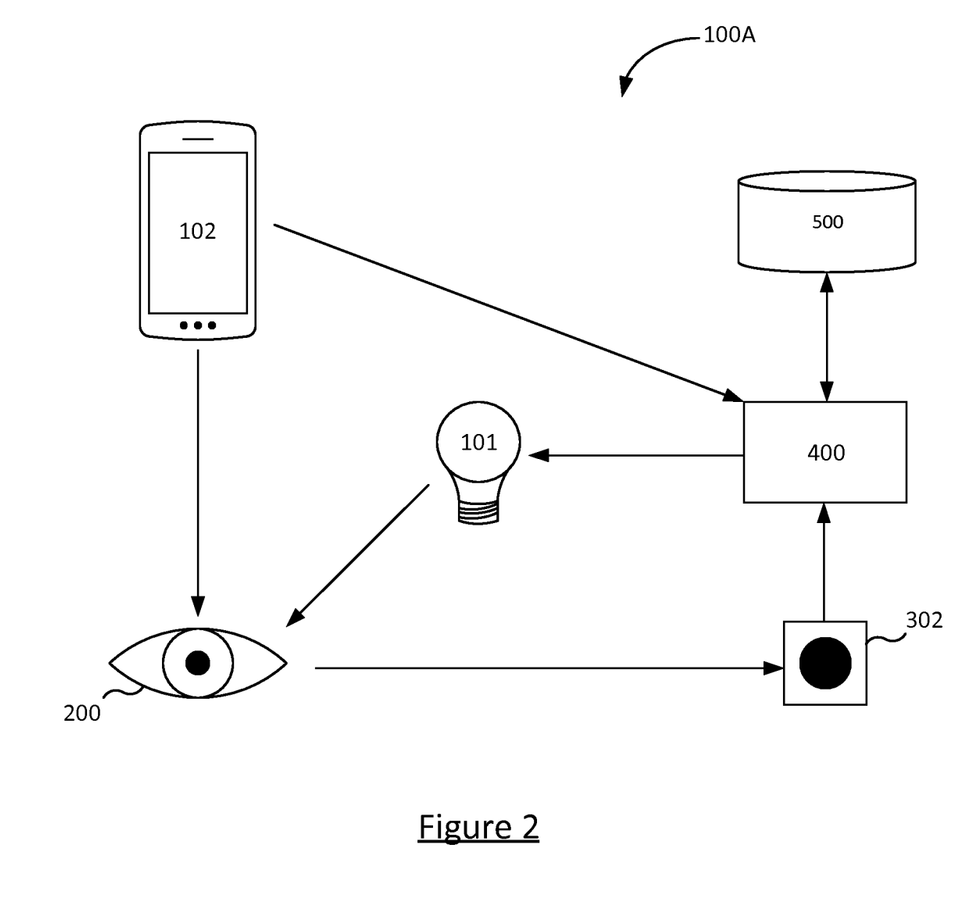
FIG. 2 shows another system according to embodiments of the present invention.

FIG. 2 shows an alternative system which does not comprise the light sensor 301. Instead, information pertaining to the second light source 102 (e.g. information indicating the type of device the second light source 102 is built into) is received by the controller 400 and then used by the controller 400 to retrieve information about the light output of the second light source 102 from a memory such as database 500 shown in FIG. 2. The database 500 may be an external database accessible over a network or may be an internal memory of the controller 400 itself. That is, rather than measuring the light falling onto the eye 200, the controller 400 uses the database 500 to find out what the spectrum of the second light source 201 is. When the second light source 201 is part of a computing device, e.g. when the second light source 201 is a screen of a tablet or mobile device, then it is assumed that the user 600 is looking into the light source 201 if the device is turned on or active or at least that some light from the second light source 201 is entering the eye 200 of the user. Whether the device is active or not can be gauged by checking WiFi activity or the presence of a Bluetooth signal of the device, as is known in the art.

Figure 3:
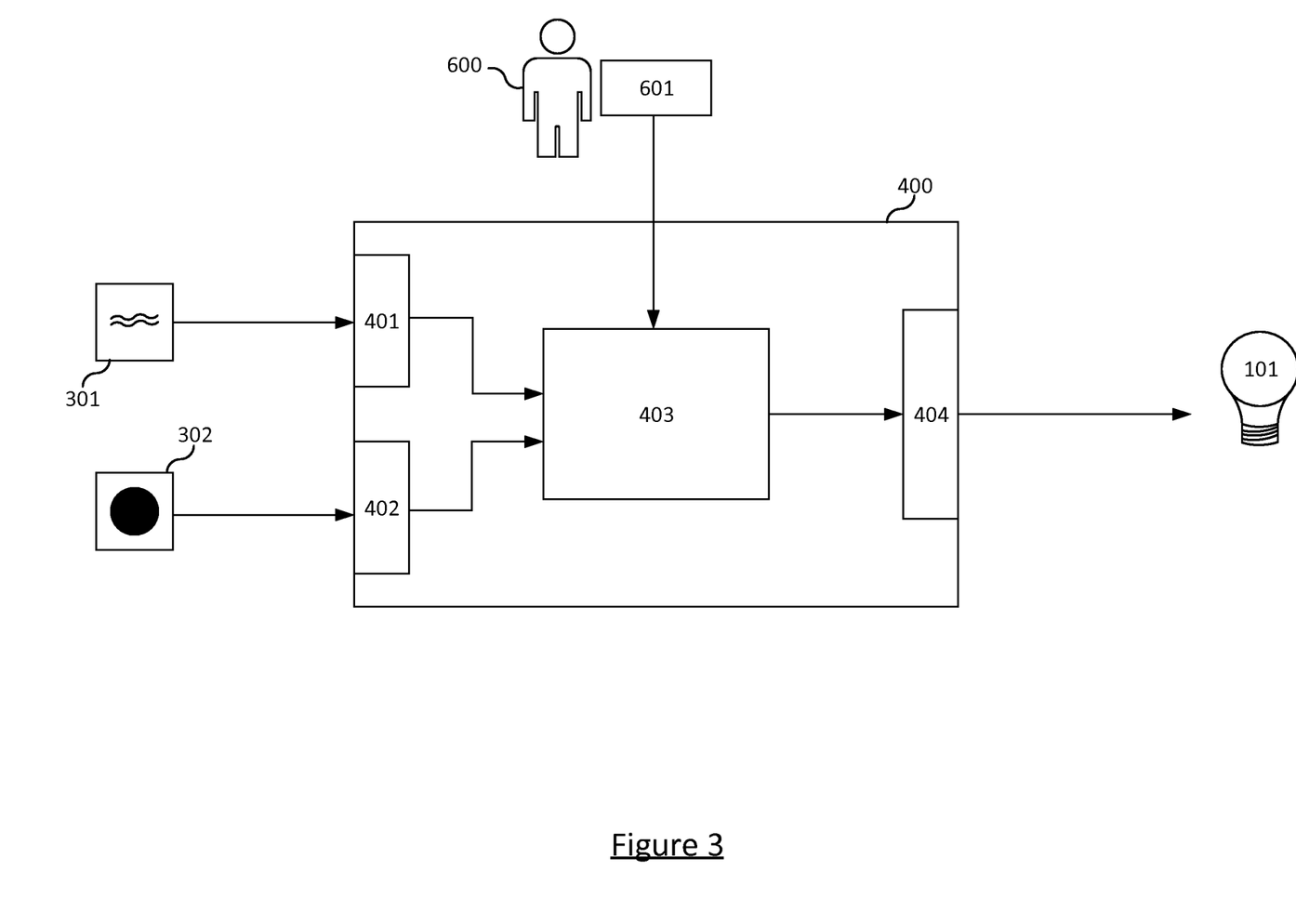
FIG. 3 is a schematic diagram of a controller according to embodiments of the present invention.

FIG. 3 shows a schematic diagram of the controller 400. The controller comprises a first input 401, a second input 402, a processor 403, and an output 404. The controller 400 may also comprise an internal memory (not shown). FIG. 3 also shows the user 600 and a user device 601 of the user 600 (e.g. a mobile device or other computing device) which may be used, as described above, by the user 600 to provide an indication of whether or not a particular biological effect is wanted or unwanted.

The first input 401 is configured to receive light property data indicating a property of the light from the second light source, said property being of a type which causes a biological effect on the human user. As in FIG. 1, this may comprise receiving light property data which were sensed directly by light sensor 301 (this is shown in FIG. 3) or, as shown in FIG. 2, this may comprise retrieving light property data from database 500 (this is not shown in FIG. 3). Anyway, when the properties of the light from the second light source 102 are determined, the controller 400 is able to determine therefrom whether or not the light will have a biological effect on the user. The controller 400 is also able to determine whether or not this effect is wanted or unwanted by the user, based on e.g. a stored indication as mentioned above.

The second input 402 is configured to receive pupil sensor data from the pupil sensor 302 detecting a size of the pupil of the human user.

The output 404 is configured for sending control commands to the first light source 101. Methods for doing so are well-known in the art and so not described in detail here.

The processor 403 is configured to determine, using the light property data received via the first input, that the light from the second light source has said property; in response to said determination that the light from the second light source has said property, determine, using said pupil sensor data received via the second input, a current size of the pupil; and on condition that the current size of the pupil is determined to be outside of a desired range, control light output of the first light source in order to bring the pupil size inside said desired range.

Whether or not the pupil is outside of a desired range need not be determined from direct pupil size measurement but can also be inferred from other factors. For example, the determination that the pupil size is larger than a minimum size can be inferred from on the amount of ambient light present. If this light level is below a threshold, it can be assumed that the pupil is not its minimum size.

For example, the second light source 102 may be a screen of a computing device on which the user 600 is watching a video (e.g. a tablet, phone, or computer). The device may emit excessive blue light (as is common with illuminated screens) which may be unwanted, e.g. at night when the user 600 wishes to sleep shortly thereafter. The light sensor 301 may be positioned close to the user's eye 200 (e.g. integrated in a wearable device such as glasses) and detects that the spectrum of the light from the second light source 102 comprises a high amount of blue. The pupil sensor 302 may be a camera and may also be implemented in the glasses but may also be implemented in the computing device itself, such as a front-facing camera of the computing device capturing an image of the user. The controller 400 may be implemented in the computing device itself, in the glasses mentioned above, be part of the first light source 101 or be a separate controller functionally connected with input devices such as the sensors 301 and 302 described above and output devices such as the first light source 101 described above. The sensors 301, 302 and the controller 400 preferably communicate wirelessly (e.g. WiFi) but it is not excluded that they are connected via hard wired connections, or a combination of wired and wireless connections. Based on the input from the light sensor 301 and the pupil size sensor 302, the amount of light of the computing device light source (i.e. the second light source 102) is determined. If the pupil size is not yet minimal and the light is excessively blue, the amount of ambient light (i.e. the first light source 101) will be increased to reduce the pupil diameter and therewith reduce the amount of blue light received at the retina. If the pupil size is minimal (around 2 mm), adding light will not change pupil diameter anymore and consequently the amount of blue light hitting the retina cannot be further reduced.

In other embodiments, the controller 400, light sensor 301, and pupil sensor 302 are all implemented in the same physical device such as a tablet or smart phone (i.e. user device 601) operated by the user 600. Alternatively, the light sensor 301 and the pupil sensor 302 may be implemented in the user device 601 and the controller 400 implemented in an external computing device such as a server to which the sensor data are transmitted for processing. This may be particularly advantageous in embodiments where the first light source 101 is an ambient light source such as room lighting within an environment and is already controlled by a controller.

Figure 4A:
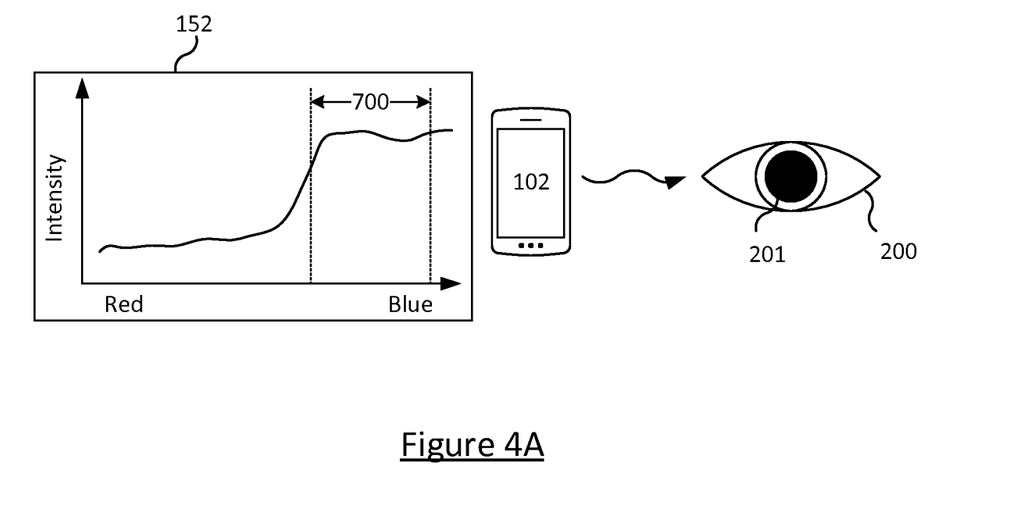
FIG. 4A shows a light source having a biological effect on a user.
Figure 4B:
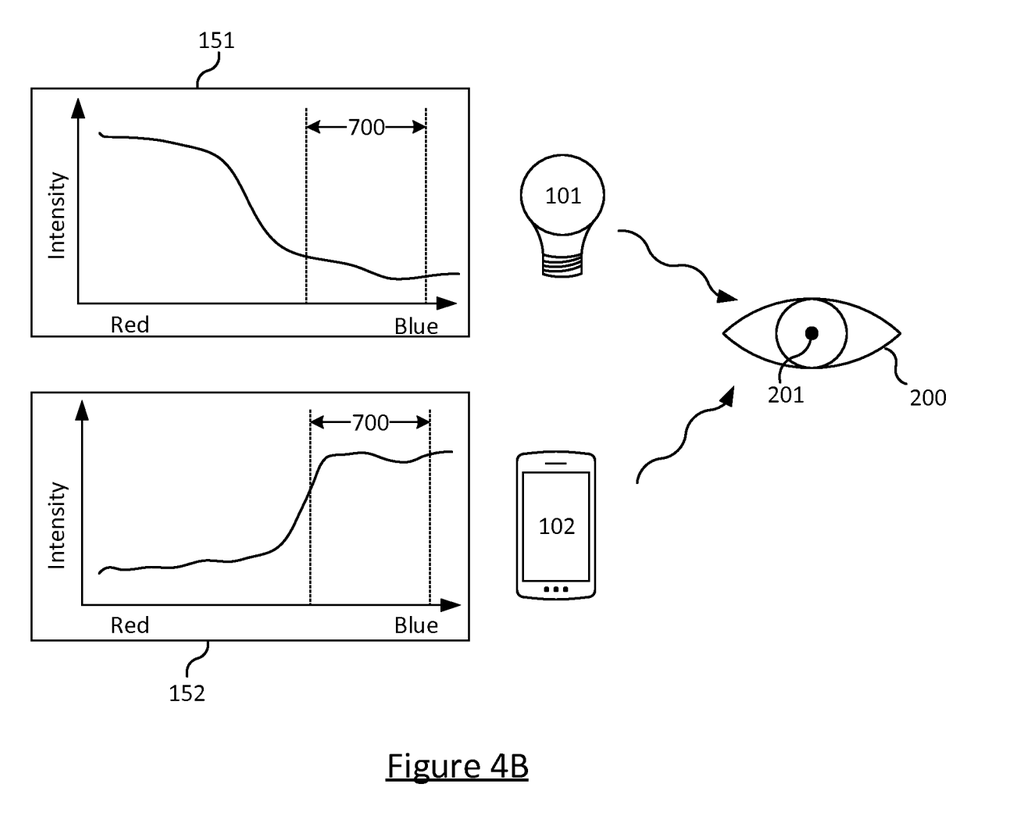
FIG. 4B shows minimization of a biological effect on a user.

FIGS. 4A and 4B illustrate one advantage of the present invention. FIG. 4A shows the incidence of light from a second light source 102 alone on the eye 200 and FIG. 4B shows the improvement offered by adding light from the first light source 101 as in the present invention.

In FIG. 4A, an example spectrum 152 of the light output by the second light source 102 is shown entering the eye 200. The spectrum 152 comprises a significant amount of power within a therapeutic window 700. The therapeutic window 700 is shown in this example as comprising blue wavelengths of light, but it is understood that different ranges of the spectrum may be of interest for different biological effects. The therapeutic window shown in FIG. 4A may, for example, be particularly effective for increasing alertness in the user 600.

The processor 403 receives information about the spectrum 152 wherein the information at least includes whether or not the light produces a biological effect, as described above. In this example, the biological effect is alertness, and the processor 403 determines that the light from the second light source 102 does indeed produce this effect on the user 600. The processor 403 further determines whether or not this effect is desired by the user 600, e.g. based on user input from user device 601 as mentioned above. This determination may also be assumed by the processor 403 based on other information. For example, the "alertness" effect may be assumed to be wanted during morning hours (e.g. 7 am-9 am) and unwanted at night (e.g. 9 pm onwards).

The processor 403 also receives information about the pupil size of the user's eye 200. In this example, the pupil 201 is large and the processor 403 determines whether or not the pupil 201 is larger than the minimum size. In this case the pupil size is larger than a minimum size, such as 2 mm for human pupils, and the alertness effect of the blue light entering the pupil 201 is unwanted by the user 600, such as explicitly specified by the user via user device 601 or as assumed because of night time.

FIG. 4B shows the same situation as FIG. 4A, but with the addition of the first light source 101 in accordance with the present invention. The first light source 101 has an output spectrum shown by spectrum 151. Notably, the first light source 101 does not output significant power within the therapeutic window 700. That is, the first light source 101 does not produce the alertness effect as the second light source 102 does.

As mentioned above, the processor 403 has determined that the second light source 102 is outputting light having a biological effect on the user 600 which is unwanted. The processor 403 has also determined that the pupil 201 is larger than the minimum size. In response to this, the processor 403 controls the first light source 101 to increase its light output, especially in the light spectrum outside the therapeutic window 700. This increases the total amount of light (i.e. combined from the first light source 101 and the second light source 102) incident on the eye 200 and therefore causes the pupil 201 to shrink. Note that here, "light output" refers to the intensity of the first light source 101, which may correlate with the perceived brightness by a human user perceiving the light.

The size of the pupil 201 has now been reduced by increasing the total amount of light provided to the user's eye 200 but without increasing the total amount of blue light (i.e. the overall optical power within the therapeutic window 700) because the additional light comprised reddish light (i.e. optical power outside the therapeutic window 700). Hence, less blue light enters the user's eye 200 in the situation of FIG. 4B than in the situation of FIG. 4A, which reduces the unwanted biological effect.

It will be appreciated that the above embodiments have been described only by way of example. Other variations to the disclosed embodiments can be understood and effected by those skilled in the art in practicing the claimed invention, from a study of the drawings, the disclosure, and the appended claims.

As a first example of such variation it is considered that modification of the first light source 101 directly based on the (total) amount of therapeutic light reaching the eye 200 may lead to unwanted oscillating behaviour in the output of this light source. E.g., when the energy in the blue part of the spectrum, as measured by a sensor, is constantly changing, the external light sources (for example the first light source 101) will constantly change their intensity and/or colour or colour temperature, i.e. shifting to lower colour temperatures or warmer colours when exposure to blue light increases and back to higher colour temperatures or cooler colours when it decreases again. To prevent the user 600 from becoming annoyed or disturbed by this behaviour, the controller 400 can set a time constant for light modifications. That is, the controller 400 can "smooth out" temporal changes to the lighting settings of the first light source 101. If a high time constant is set, the first light source 101 reacts only slowly to changes in blue content measured by the sensor, while it reacts quickly when the time constant is low.

The pupil size adjustments of a human eye are more sensitive to some wavelengths of light than others. Hence, controlling the colour temperature of the first light 101 can also be used to change the pupil size.

As a second example, the activation of the first light source 101 may be considered a "compensatory" system and may be optionally turned on and/or off by the user 600. E.g. the user device 601 may be used by the user 600 to specify when or where the compensatory light system should be active. When the compensatory system is "off", the system functions as in sub-system 110 without interaction with the first light source 101 and controller 400. When the compensatory system is "on", the system functions as described herein with the first light source 101 and controller 400 thereof being active.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored and/or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A controller for controlling a first light source to emit light into a pupil of a human user in order to reduce at least one biological effect of light from a second light source on the human user, the controller comprising:
    a first input for receiving light property data indicating a property of the light from the second light source, said property being a substantial luminance in a blue part of the visible spectrum which causes a biological effect on the human user;
    a second input for receiving pupil data indicating a size of the pupil of the human user;
    an output for sending control commands to the first light source;
    a processor configured to:
    determine, using the light property data received via the first input, that the light from the second light source has said property;
    in response to said determination that the light from the second light source has said property, determine, using said pupil data received via the second input, a current size of the pupil; and
    on condition that the current size of the pupil is determined to be larger than a minimum size, control the first light source to emit light not having said property into the pupil and thereby reduce the size of the pupil, without changing the properties of the light from the second light source.

2. The controller according to claim 1, wherein said data indicating a property of the light from the second light source is received from a light sensor detecting the property of the light from the second light source.

3. The controller according to claim 1, wherein said data indicating a property of the light from the second light source is received from a database storing properties of the second light source.

4. The controller according to claim 1, wherein the processor is arranged to perform said control of the first light source with a time constant specifying a transition time from a first light output setting of the first light source to a second light output setting of the first light source.

5. The controller according to claim 1, wherein the second light source is a screen of a computing device.

6. The controller according to claim 1, wherein the second light source is a luminaire arranged to illuminate an environment of the human user.

7. The controller according to claim 1, wherein the pupil data are received from a pupil sensor detecting the size of the pupil of the human user.

8. The controller according to claim 7, wherein the pupil sensor is a camera arranged to capture an image of the pupil of the human user.

9. The controller according to claim 8, wherein the camera is integrated into a user device of the human user.

10. A user device comprising the controller according to claim 8 and the camera, wherein the camera is a front-facing camera integrated into the user device.

11. The user device according to claim 10, wherein the first light source is a light source separate from the user device.

12. A system comprising the user device according to claim 10 and the first light source.

13. A method of controlling a first light source to emit light into a pupil of a human user in order to reduce at least one biological effect of light from a second light source on the human user, the method comprising:
    receiving light property data indicating a property of the light from the second light source, said property being a substantial luminance in a blue part of the visible spectrum which causes a biological effect on the human user;
    receiving pupil data indicating a size of the pupil of the human user;
    determining, using the light property data, that the light from the second light source has said property;
    in response to said determination that the light from the second light source has said property, determine, using said pupil data, a current size of the pupil; and
    on condition that the current size of the pupil is determined to be larger than a minimum size, controlling the first light source to emit light not having said property into the pupil and thereby reducing the size of the pupil, without changing the properties of the light from the second light source.

14. The method of claim 13 wherein the method further comprises providing the first light source in proximity of the human user or the human user's eye(s).

15. A computer program product comprising computer-executable code embodied on a computer-readable storage medium arranged so as when executed by one or more processing units to perform the method according to claim 14.

* * * * *